United States Patent [19]

Shorter et al.

[11] Patent Number: 4,645,508
[45] Date of Patent: Feb. 24, 1987

[54] ARTIFICIAL ANKLE JOINT

[75] Inventors: John J. Shorter; Stanley T. Early, both of Basingstoke, England

[73] Assignee: Chas. A. Blatchford & Sons Limited, Hampshire, England

[21] Appl. No.: 753,639

[22] Filed: Jul. 10, 1985

[30] Foreign Application Priority Data

Jul. 11, 1984 [GB] United Kingdom ............... 8417630

[51] Int. Cl.⁴ .............................................. A61F 2/66
[52] U.S. Cl. ................................................. 623/48
[58] Field of Search ................... 403/135, 140, 122; 623/23, 49, 47, 48

[56] References Cited

U.S. PATENT DOCUMENTS 4,380,090  4/1983  Ramos .................................. 623/23

FOREIGN PATENT DOCUMENTS 2070439  9/1981  United Kingdom ................... 623/49
2084025  4/1982  United Kingdom ................... 623/49
2110936  6/1983  United Kingdom ................... 623/49

OTHER PUBLICATIONS

*Amputation and Prostheses*—A Survey in North-West Europe and North America, date: 1968, Authors: G. E. Fulford and M. J. Hall (paragraph 4, pp. 38-39).

Primary Examiner—Richard J. Apley
Assistant Examiner—James Prizant
Attorney, Agent, or Firm—Barnes & Thornburg

[57] ABSTRACT

An artificial ankle joint (FIG. 1) is of the kind which connects a shin member to a foot, by means of a ball and socket joint. The socket has adjacent main and subsidiary socket portions. The main socket portion has a first part, which engages the elastic covering of the ball, and a second part which extends down from the first part and receives within it the subsidiary socket portion. A circlip locks the parts together. The main socket portion includes an integral skirt which engages an annular elastic buffer which is mounted around the ball shank.

12 Claims, 4 Drawing Figures

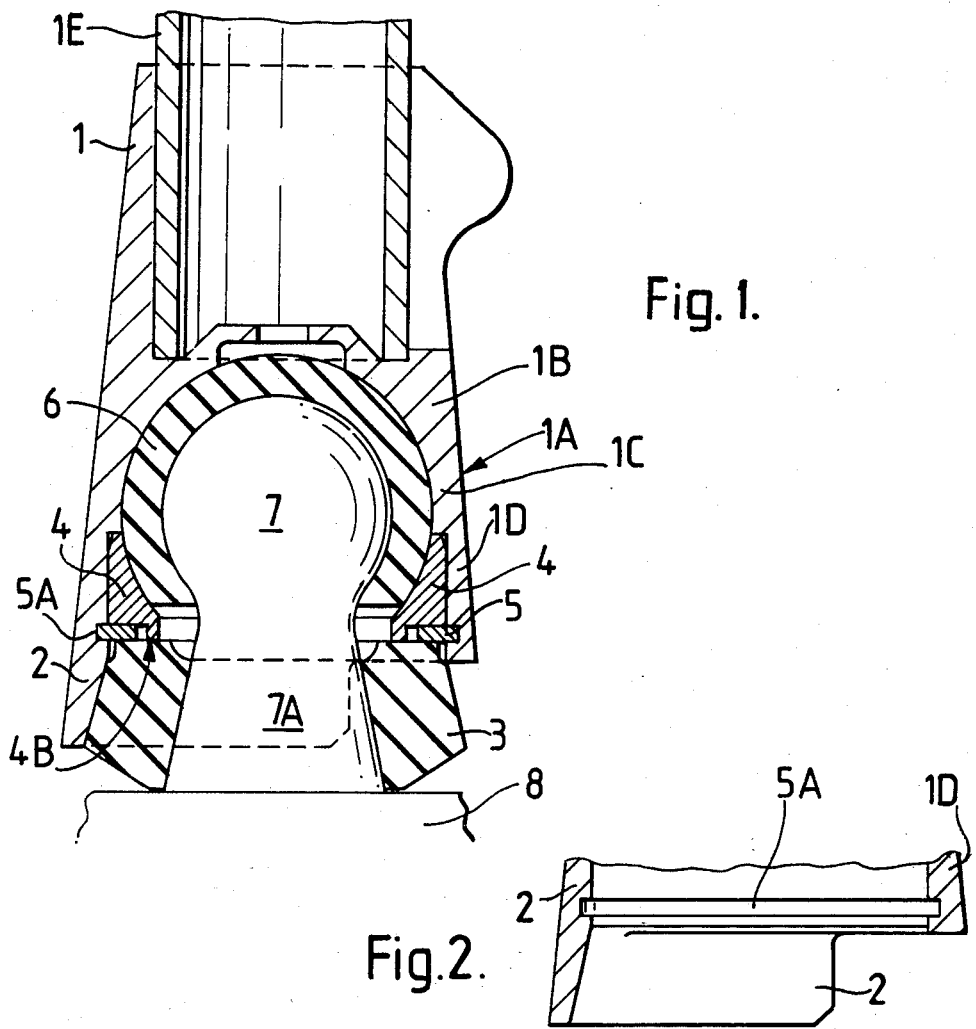
Fig. 1.
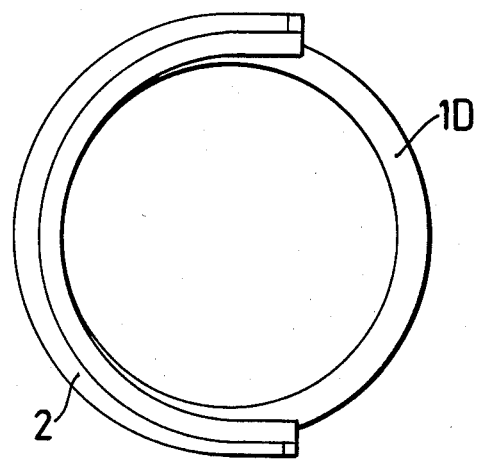
Fig. 2.
Fig. 3.

ARTIFICIAL ANKLE JOINT

FIELD OF THE INVENTION

This invention relates to an artificial leg having a shin member, a foot, and a ball and socket joint connecting the shin member and foot.

DESCRIPTION OF THE PRIOR ART

In a known kind of such an artificial leg, the ball and socket joint constitutes in effect an ankle; the ball is partspherical and may be encased in a matching partspherical cover of rubber or polyurethane or other elastic material over which the socket is fixed. This known kind of artificial leg permits limited cushioned flexion of shin and foot, to give dorsi-flexion and plantar-flexion of the foot, and also medial and lateral flexion. "Dorsi-flexion" is upward movement of the fore-part of the foot relative to the shin, whilst "plantar-flexion" is downward movement of the fore-part of the foot relative to the shin. In addition this known kind of artificial leg also permits limited relative rotation of the shin relative to the foot about the vertical axis of the shin.

It has been found desirable, in such an artificial leg, to provide (i) relatively greater resistance to dorsi-flexion whilst permitting relatively lower resistance to plantar-flexion; and (ii) means by which the foot is readily replaceable and removable, and also by which the position or angle of the foot may be readily adjustable relative to the shin.

In prior British Patent Specification No. 2,084,025A there is disclosed an artificial leg of the known kind mentioned above, wherein the socket of the ball and socket joint has upper and lower socket portions which fit around the ball, the upper socket portion being connected to the shin member and the two socket portions being connected together by, and clamped around the ball by, a rotatable sleeve-like member which, on rotation in one direction, causes the two socket portions to move towards each other to clamp the ball.

In British Patent Specification No. 2,110,936A there is disclosed an artificial leg of the known kind mentioned above, in which the ball has a ball portion within the socket and a coupling shank, wherein the socket includes an extension arranged to co-operate with an elastic buffer mounted between the coupling shank and the extension so as to provide resistance to dorsi-flexion of the foot relative to the shin member. The elastic buffer is preferably a thick rubber ring fitting over the coupling shank by which the latter may be fixed to and upstands from, the foot. The extension of the socket preferably only partly surrounds the rubber ring so as to engage it at the front and sides, but not at the back.

SUMMARY OF THE INVENTION

An object of the present invention is to provide an artificial leg of the known kind mentioned above, which has an ankle joint of improved construction, such that it is easier and less expensive to manufacture, easier to assemble, and better in appearance than previous constructions.

According to one aspect of this invention, there is provided an artificial leg of the known kind mentioned above, wherein the socket has adjacent main and subsidiary socket portions, the main socket portion having a first part which engages the ball, or the elastic covering thereon if provided, and a second part which extends beyond the first part and which receives the subsidiary socket portion, and wherein the socket includes a connecting device whereby the subsidiary socket portion is retained within the second part of the main socket portion and whereby the main and subsidiary socket portions are together clamped on the ball, or the elastic covering if provided.

Preferably the main socket portion is an outer, upper socket portion enveloping an upper part of the covering and the ball, and the subsidiary portion is an inner, lower socket portion enveloping a lower part of the covering and the ball. Preferably also the second part of the main socket portion extends downwards to a level below a bottom surface of the lower socket portion, with the connecting device in the form of a circlip engaging the said bottom surface and also the said second part, in such manner as to retain the outer and inner socket portions together against the upper and lower parts respectively of the elastic covering and the ball. The first part of the main socket portion preferably has an integral upward extension by which the foot may be connected to a shin member. For example, the integral upward extension may be formed with an upwardly directed tubular socket in which may be received and fixed the lower end of a shin tube. It is also preferred that the second part of the main socket portion has an integral downward extension which co-operates with an elastic buffer which is mounted between a downwardly extending coupling shank of the ball and the integral downward extension so as to provide resistance to dorsi-flexion of the foot relative to the shin member.

BRIEF DESCRIPTION OF THE DRAWINGS

One embodiment of the invention will now be described by way of example with reference to the drawings, in which:

FIG. 1 is a schematic central vertical section of one embodiment of an ankle joint in accordance with the invention;

FIG. 2 is a detail central vertical section showing the lower end of the second part of the main socket portion;

FIG. 3 is an underneath plan view of FIG. 2; and

DESCRIPTION OF THE PREFERRED EMBODIMENTS

Figure 4:
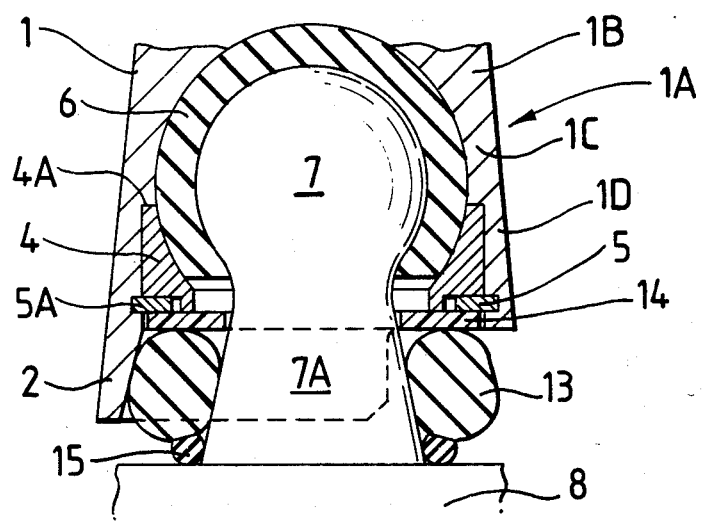
FIG. 4 is a schematic part central vertical section of another embodiment.

Referring to the drawing, an ankle joint has a socket indicated generally by the reference number 1A, the socket having a main socket portion 1B and an adjacent subsidiary socket portion 4. The main socket portion 1B has a first part 1C which engages a covering 6 of rubber or polyurethane or other elastic material around a ball 7. The ball is integral with a coupling shank 7A by which the ball is mounted on a foot, part of which is indicated at 8. The main socket portion 1B also has a second part 1D which extends down beyond the first part of 1C and which receives within it the subsidiary socket portion 4. The socket 1A also has a connecting device in the form of a circlip 5 which when in position in an annular slot 5A of the second part 1D, retains the subsidiary socket portion 4 in the main socket portion 1B. In this way the two socket portions 1B and 4 are clamped round the ball and its elastic covering. Preferably the socket portion 4 is bonded in the part 1D.

The main socket portion 1B has (i) an integral upward extension 1, which provides a tubular socket to receive for example the lower end of a shin tube 1E, and (ii) an integral downward extension 2. Also seen in FIG. 1 is an elastic buffer 3, which will be referred to below.

In the present embodiment the main socket portion 1B is an outer, upper socket portion enveloping an upper part of the covering 6 and ball 7 as shown, while the subsidiary portion 4 is an inner, lower socket portion enveloping a lower part of the covering and ball. The second part 1D of the main socket portion extends downwards to a level below the bottom surface 4B of the subsidiary portion 4, and has the slot 5A in which is springingly received the circlip 5.

The integral downward extension 2 is in the form of a skirt which extends around the front and sides, but not around the back, see also FIGS. 2 and 3. The extension or skirt 2 co-operates with the elastic buffer 3 which is annular, is of the frusto-conical cross-sectional shape shown, and is mounted around the shank 7A, and between it and the skirt 2. Dorsi-flexion is restricted by the buffer 3 when the skirt 2 presses rearwardly against it.

The subsidiary socket portion 4 is a ring which is a tight push or press fit in the main portion 1B, where it is held in place by the circlip 5. The latter can only be fitted into its slot 5A when the parts 1B and 4 are properly together and clamping the ball and its covering.

FIG. 4 shows another embodiment, in which the annular buffer 3 of FIG. 1 is replaced by an annular buffer 13 of toroidal cross-section. The longer axis of that cross-section is generally parallel to the axis of the shank 7A. Between the circlip 5 and subsidiary socket portion 4, on the one hand and the buffer 13 on the other, is disposed an annular washer 14, preferably made of plastics material. Also between the buffer 13 and the foot 8 is an O-ring 15.

As will be understood from FIGS. 1 and 4, the ankle joint of the invention has a simple and uncluttered exterior shape, has relatively few parts, and is relatively simple to assemble.

We claim:

1. An artificial leg having a shin member, a foot, and a ball and socket joint connecting the shin member and foot, wherein:
   (i) the socket has main and subsidiary socket portions, the main socket portion having a first part which engages the ball or the elastic covering thereon if provided, and a second part integral with the first part, the second part extending beyond the first part and within which second part the subsidiary socket portion is received;
   (ii) the socket includes connecting means within the second part whereby the subsidiary socket portion is retained within the second part of the main socket portion and whereby the main and subsidiary socket portions are together clamped on the ball or the elastic covering thereon if provided;
   (iii) the main socket portion is an outer upper socket portion enveloping an upper part of the ball and covering if provided, and the subsidiary socket portion is an inner, lower socket portion enveloping a lower part of the ball and covering if provided.

2. An artificial leg according to claim 1 wherein the main socket portion includes an integral upward extension adapted to connect the foot to the lower end of a shin member.

3. An artificial leg according to claim 2 wherein the main socket portion includes an integral extension arranged to co-operate with an elastic buffer which is mounted between a downwardly extending coupling shank of the ball and the lower extension so as to provide resistance to dorsi-flexion of the foot relative to the shin member.

4. An artificial leg according to claim 3 wherein the integral downward extension is of skirt-like form and is U-shaped in cross-section.

5. An artificial leg according to claim 3 wherein the elastic buffer is annular, surrounds the coupling shank, and is in engagement with the integral downward extension.

6. An artificial leg according to claim 5 wherein the elastic buffer is of toroidal cross section.

7. An artificial leg according to claim 6 wherein a washer of plastics material is disposed between the elastic buffer and the subsidiary socket portion.

8. In an artificial leg having a shin member and a foot, an improved ball and socket joint for connecting the shin member and foot, the joint comprising:
   a ball and a coupling shank for coupling the ball to a foot such that the ball is situated above the foot, an inverted cup-shaped main socket for attachment to the shin having a first portion enveloping at least an upper portion of the ball, a second portion integral with the first portion extending downward from a lower perimeter of the first portion, and including a step and inner wall defining a sleeve, an annular subsidiary socket surrounding at least a lower portion of the ball and received within the sleeve, the subsidiary socket having an upper surface confronting the step, and connecting means for retaining the subsidiary socket within the sleeve of the main socket to clamp the ball between the main and subsidiary sockets.

9. An improved ball and socket joint according to claim 8 wherein the ball further comprises an outer surface composed of an elastic material, the outer surface intimately contacting an inner surface of both the main and subsidiary sockets.

10. An improved ball and socket joint according to claim 8 wherein the ball is integral with the coupling shank, the coupling shank having a conical outer surface, the diameter of the upper most portion of the coupling shank being less than the diameter of the ball.

11. An improved ball and socket joint according to claim 8 wherein the connecting means includes a circlip which engages a bottom surface of the subsidiary socket portion and also engages the second part of the main socket portion, in such manner as to retain the main and subsidiary socket portions against upper and lower parts respectively of the ball and covering.

12. An improved ball and socket joint according to claim 11 wherein the subsidiary socket is bonded to the sleeve.

* * * * *